United States Patent [19]

Powell

[11] 4,052,388
[45] Oct. 4, 1977

[54] 3-ACETYLTETRAHYDRO-2-(NITROME-THYLENE)-2H-1,3-THIAZINE

[75] Inventor: James E. Powell, Modesto, Calif.

[73] Assignee: Shell Oil Company, Houston, Tex.

[21] Appl. No.: 731,147

[22] Filed: Oct. 12, 1976

[51] Int. Cl.$^2$ .......................................... C07D 279/06
[52] U.S. Cl. ...................................... 544/54; 424/246
[58] Field of Search ..................................... 260/243 R

[56] References Cited

U.S. PATENT DOCUMENTS 3,993,648    11/1976    Powell ................................. 260/243

*Primary Examiner*—John M. Ford

[57] ABSTRACT

The title compound, useful as an insecticide.

1 Claim, No Drawings

3-ACETYLTETRAHYDRO-2-(NITROMETHYLENE)-2H-1,3-THIAZINE

DESCRIPTION OF THE INVENTION

It has been found that useful insecticidal activity is possessed by 3-acetyltetrahydro-2-(nitromethylene)-2H-1,3-thiazine, which can be described by the general formula

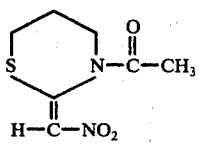

The compound of the invention can be prepared as follows:

A solution of 23 g of 1-nitro-1-(tetrahydro-2H-1,3-thiazin-2-ylidene)-2-pentanone (Example 5, U.S. Pat. No. 3,962,225) in 200 ml of monoglyme was added dropwise at 0° C to a suspension of 4.65 g of a 57% sodium hydride/mineral oil dispersion in 100 ml of monoglyme. The stirred mixture was allowed to warm to room temperature and stirred overnight. A solution of 8.2 g of acetyl chloride in 50 ml of monoglyme was added dropwise to the reaction mixture at 0° C. The resulting mixture was stirred for one hour at 0° C, then allowed to warm to room temperature and stirred for 30 minutes. The mixture was diluted with chloroform and extracted with 10% sodium hydroxide solution. The organic phase was separated, washed with water, then with saturated sodium chloride solution, and dried ($Na_2SO_4$), and the solvent was evaporated under reduced pressure. The resulting liquid was chromatographed, using a wet column with silica gel. As eluent, there was first used 2 liters of a 98/2 chloroform/acetone mixture, then a 95/5 chloroform/acetone mixture was used. Three fractions were obtained. The last fraction was triturated with ether, then cooled, to give a solid yellow product, the compound of this invention, m.p.: 91° – 92.5° C. The identity of the product was confirmed by appropriate chemical and spectral analyses.

The compound of this invention exhibits useful insecticidal activity, being of particular interest for control of the larvae "caterpillar" or "worm" forms of insects of the genus *Heliothis*, such as *H. Zea* (corn earworm, cotton bollworm, tomato fruitworm), *H. virescens* (tobacco budworm); the genus *Agrotis*, such as *A. ipsilon* (black cut-worm); the genus *Trichoplusia*, such as *T. ni* (cabbage looper), and the genus *Spodoptera*, such as *S. littoralis* (Egyptian cotton leafworm). It also is of interest for controlling aphids and houseflies. In tests that have been conducted it has exhibited low, or no, toxicity to other insects such as the 2-spotted spider mite and mosquito larva. It acts rapidly on corn earworm larvae, houseflies and pea aphids, providing "quick knockdown" of these insects.

Activity of the compound of this invention with respect to insects was determined by using standardized tests to establish the $LC_{50}$ dosage (in milligrams of test compound per 100 milliliters of solvent or liquid carrier required in the solution or suspension of the compound) that was required to kill 50% of the test insects. The test insects were the housefly, corn earworm, mosquito, pea aphid and 2-spotted spider mite.

The compound was found to be inactive or but slightly active with respect to the mites and mosquito larvae. It was found to be highly active with respect to the corn earworms and moderately active with respect to the pea aphids and houseflies.

In the course of these tests it was noted that the compound acted quickly on the houseflies, pea aphids and corn earworms.

The invention includes within its scope insecticidal compositions comprising an adjuvant — that is, a carrier optionally a surface-active agent — and, as active ingredient, the compound of this invention. Likewise the invention includes also a method of combatting insect pests at a locus which comprises applying to the locus an effective amount of the compound of the invention.

The term "carrier" as used herein means a material which may be inorganic or organic and of synthetic or natural origin with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as for example, coumarone resins, polyvinyl choride and styrene polymers and copolymers, solid polychlorophenols; bitumen, waxes such as beeswax, paraffin wax and chlorinated mineral waxes; degradable organic solids such as ground corn cobs and walnut shells and solid fertilizers, for example, superphosphates.

Suitable liquid carriers include solvents for the compounds of this invention and liquids in which the toxicant is insoluble or only slightly soluble.

Examples of such solvents and liquid carriers generally are water, alcohols, for example, isopropyl alcohol, ketones, such as acetone, methyl ethyl ketone, methyl isobutyl ketone and cyclohexanone; ethers, aromatic hydrocarbons, such as benzene, toluene and xylene; petroleum fractions, such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkyaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of toxicant. Granules may be manufactured by agglomeration or impregnation techniques. Generally, granules will contain ½–25%w toxicant and 0–10%w of additives such as stabilizers, slow release modifiers and binding agents. Emulsifiable concentrates usually contain, in addition to the solvent, and when necessary, co-solvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size or particles, the insect species to be controlled and the like, proper consideration and resolution of these factors to provide the necessary dosage of active material at the locus being within the skill of those versed in the art. In general, however, the effective dosage of toxicants of this invention at the locus to be protected — i.e. the dosage to which the insect contacts — is of the order of 0.001% to 0.5% based on the total weight of the formulation, though under some circumstances the effective concentration will be as little as 0.0001% or as much as 2%, on the same basis.

I claim:
1. 3-acetyltetrahydro-2-(nitromethylene)-2H-1,3-thiazine.

* * * * *